(12) United States Patent
Hwang et al.

(10) Patent No.: US 7,022,875 B2
(45) Date of Patent: Apr. 4, 2006

(54) THIOBUTACIN AND ANTIFUNGAL AND ANTIOOMYCETE COMPOSITION FOR CONTROLLING PLANT DISEASES USING THE SAME

(75) Inventors: Byung Kook Hwang, Seoul (KR); Jung Yeop Lee, Seoul (KR)

(73) Assignee: Korea University Industry and Academy Cooperation Foundation, Seoul (KR)

( * ) Notice: Subject to any disclaimer, the term of this patent is extended or adjusted under 35 U.S.C. 154(b) by 196 days.

(21) Appl. No.: 10/756,683

(22) Filed: Jan. 13, 2004

(65) Prior Publication Data

US 2004/0180960 A1 Sep. 16, 2004

(30) Foreign Application Priority Data

| Mar. 13, 2003 | (KR) | 10-2003-0015629 |
| Mar. 13, 2003 | (KR) | 10-2003-0015628 |

(51) Int. Cl.
C07C 229/00 (2006.01)

(52) U.S. Cl. ........................ 562/433; 562/400; 562/405; 562/426; 435/41

(58) Field of Classification Search ................. 562/405, 562/426, 433; 435/41
See application file for complete search history.

(56) References Cited

OTHER PUBLICATIONS

Vazquez et al, Journal of Biological Chemistry (2002) 277 (77) pp. 4867–4873.*

Hwang, Byung Kook, et al. "Phytophthora Blight of Pepper and its Control in Korea." Plant Disease, (1995), pp. 221–227.

Kim, Beom Seok, et al. "Biofungicides." *Fungal Biotechnology in Agricultural, Food, and Environmental Applications*, vol. 21, Marcel Dekker, Inc., pp. 123–133.

Lee, Jung Yeop, et al. "Diversity of antifungal actinomycetes in various vegetative soils of Korea," Canadian Journal of Microbiology, (2002), vol. 48, pp. 407–417.

Weisburg, William G., et al. "16S Ribosomal DNA Amplification for Phylogenetic Study." Journal of Bacteriology, (1991), vol. 173, No. 2, pp. 697–703.

Labeda, D.P., et al. "Revival of the genus *Lentza* and proposal for *Lechevalieria* gen. nov." International Journal of Systematic and Evolutionary Microbiology, (2001) vol. 51, pp. 1045–1050.

Igarashi, Masayuki, et al. "Formamicin, a Novel Antifungal Antibiotic Produced by a Strain of *Saccharothrix* sp." The Journal of Antibiotics, (1997), pp. 926–931.

Nishio, Maki, et al. "Karnamicin, A Complex of New Antifungal Antibiotics." The Journal of Antibiotics, (1989), pp. 852–868.

Horan, Ann C., et al. "A Family of Novel Macrocyclic Lactones, the Saccharocarcins Produced by *Saccharothrix aerocolonigenes* subsp. *antibiotica*." The Journal of Antibiotics, (1997), vol. 50, No. 2, pp. 119–125.

Lam, Kin Sing, et al. "Production, Isolation and Structure Determination of Novel Fluoroindolocarbazoles from *Saccharothrix aerocolonigenes* ATCC 39243." The Journal of Antibiotics, (2001) vol. 54, No. 1, pp. 1–9.

Takahashi, Eisaku, et al. "Phosphonothrixin, a Novel Herbicidal Antibiotic Produced by *Saccharothrix* sp. ST–888." The Journal of Antibiotics, (1995), vol. 48, No. 10, pp. 1124–1129.

Singh, M.P., et al. "Saccharomicins, Novel Heptadecaglycoside Antibiotics Produced by *Saccarothrix espanaenis*: Antibacterial and Mechanistic Activities." Antimicrobial Agents and Chemotherapy, (2000), p. 2154–2159.

Nonomura, Teruo, et al. "Algicidal effect of 3–(3–indolyl)butanoic acid, a control agent of the bacterial with pathogen, *Ralstonia solanacearum*." Crop Protection (2001), vol. 20, pp. 935–939.

Yoshimura, H., et al. "Alpha–Amino acids from a mushroom, *Amanita castanopsidis Hongo*, with growth–inhibiting activity." Phytochemistry (1999), vol. 52, pp. 25–27.

* cited by examiner

*Primary Examiner*—Cecilia J. Tsang
*Assistant Examiner*—Hector M. Reyes
(74) *Attorney, Agent, or Firm*—Steven J. Hultquist; Marianne Fuierer; Tristan A. Fuierer (57) ABSTRACT

A novel antibiotic thiobutacin, obtainable from *Lechevalieria aerocolonigenes* strain VK-A9, and antifungal and antioomycete compositions comprising thiobutacin as an active ingredient for control of plant diseases, e.g., those attributable to pathogens such as *Phytophthora capsici* and *Botrytis cinerea*.

14 Claims, 7 Drawing Sheets

SEQUENCE LISTING

<160> NUMBER OF SEQ ID NOS: 1

<210> SEQ ID NO 1
<211> LENGTH: 1488
<212> TYPE: DNA
<213> ORGANISM: Lechevalieria aerocolonigenes

<400> SEQUENCE: 1

```
aacgcggctc aggacgaacg ctggcggcgt gcttaacaca tgcaagtcga gcggtaaggc      60
ccttcggggt acacgagcgg cgaacgggtg agtaacacgt gggtaacctg ccctgtactc     120
```

```
tgggataagc cttggaaacg aggtctaata ccggatacga cccttgaagg catatttgag      180
ggtggaaagt tccggcggta tgggatggac ccgcggccta tcagcttgtt ggtggggtaa      240
tggcctacca aggcgacgac gggtagccgg cctgagaggg tgaccggcca cactgggact      300
gagacacggc ccagactcct acgggaggca gcagtgggga atattgcaca atgggcgaaa      360
gcctgatgca gcgacgccgc gtgagggatg acggccttcg ggttgtaaac ctctttcagc      420
agggacgaag cgcaagtgac ggtacctgca gaagaagcac cggctaacta cgtgccagca      480
gccgcggtaa tacgtagggt gcgagcgttg tccggaatta ttgggcgtaa agagctagta      540
ggcggtttgt cgcgtcggcc gtgaaaactt ggggcttaac cccgagcctg cggtcgatac      600
gggcagactt gagttcggca ggggagactg gaattcctgg tgtagcggtg aaatgcgcag      660
atatcaggag gaacaccggt ggcgaaggcg ggtctctggg ccgatactga cgctgaggag      720
cgaaagcgtg gggagcgaac aggattagat accctggtag tccacgccgt aaacggtggg      780
tgctaggtgt gggggacttc cacgttctcc gtgccgcagc taacgcatta agcacccgc       840 ctggggagta cggccgcaag gctaaaactc aaaggaattg acggggcccc gcacaagcgg      900
cggagcatgt ggattaattc gatgcaacgc gaagaacctt acctgggctt gacatgcact      960
ggaaaccggt agagatatcg gcccccttgt ggcggtgta  caggtggtgc atggctgtcg     1020
tcagctcgtg tcgtgagatg ttgggttaag tcccgcaacg agcgcaaccc tcgttccatg     1080
ttgccagcgc gttatggcgg ggactcatgg gagactgccg gggtcaactc ggaggaaggt     1140
ggggatgacg tcaagtcatc atgccccta  tgtccagggc ttcacacatg ctacaatggc     1200
cggtacaaag ggctgcgaaa ccgtgaggtg gagcgaatcc cataaagccg gtctcagttc     1260
ggatcggggt ctgcaactcg acccgtgaa  gtcgagtcg  ctagtaatcg cagatcagca     1320
acgctgcggt gaatacgttc ccgggccttg tacacaccgc ccgtcacgtc acgaaagtcg     1380
gtaacacccg aagcccgtgg ctcaacccgc aaggggaga  gcggtcgaag gtgggactgg     1440
cgattgggac gaagtcgtaa caaggtagcc gtaccggaag gttattat                  1488
```

THIOBUTACIN AND ANTIFUNGAL AND ANTIOOMYCETE COMPOSITION FOR CONTROLLING PLANT DISEASES USING THE SAME

CROSS REFERENCE TO RELATED APPLICATIONS

Priority herby is claimed under the provisions of 35 U.S.C. 119 to Korean Patent Application No. 10-2003-0015628 filed Mar. 13, 2003 and Korean Patent Aplication No. 10-2003-0015628 filed Mar. 13, 2003.

FIELD OF THE INVENTION

The present invention relates to the novel antibiotic thiobutacin and the antifungal and antioomycete composition for control of plant diseases using the same and more particularly, to thiobutacin isolated from actinomycete *Lechevalieria aerocolonigenes* strain VK-A9 and a natural antifungal and antioomycete composition for conferring protection against plant pathogen infections using the same.

BACKGROUND OF THE INVENTION

Microbial secondary metabolites not only can deter the invasion of pathogens but also have key roles in the development of agricultural antibiotics. Microbial antibiotics have a high biodegradability since they are naturally biosynthesized antibiotics. Thus, they lower the toxicity damaging to ecosystem as well as decrease harmful effects, such as destruction of ecosystem and pollution.

Further, the use of naturally accruing microbial secondary metabolites reduces appearances of chemical-resistant strains of pathogens and casualties to soil, humans and animals associated with organic-synthesized agricultural fungicides having various chemical structures and biological functions.

Blasticidin S is the first agricultural antibiotic isolated from actinomycete strain *Streptomyces* for the control of rice blast. Since the production of Blasticidin S, the use of antibiotics in plant protection has highly involved the production of microorganic secondary metabolites. As a result, kasugamycin, validamycin A, polyoxin derivatives, mildiomycin and the like have been developed and being used for the control of various plant diseases.

Microbial antibiotics themselves have been used as fungicides and as a lead for developing agricultural fungicides. Examples of such microbial antibiotics include commercialized β-methoxyacrylates azoxystrobin and kresoxim-methyl developed from strobilurin which is an antibiotic isolated from Basidiomycota. Other agricultural fungicides, feniclonil and fludioxonil, are developed from an antibiotic pyrrolnitrin isolated from Pseudomonas.

Among microbial secondary metabolites, some recently exhibit agricultural antifungal activity against various plant pathogen infections which are not confirmed. For example, gopalamycin, tubercidin, manumycin-type antibiotics, oligomycin A, streptimidone, daunomycin, and phenylacetic acid are confirmed to have control efficacy against various plant diseases.

Studies on secondary metabolites isolated from microorganisms inhabiting various different environments have been conducted. Particularly, since actinomycetes produce antibiotic compounds having diverse chemical structures, such as aminoglycosides, anthracyclines, glycopeptides, β-lactams, macrolides, nuclocides, peptides, polyenes, polyethers, tetracyclines, and the like, developments of physiologically active compounds including antibiotic compounds have been carried out.

Some species of *Saccharothrix*, one of the rare actinomycete genera designated as non-*Streptomyces,* have been renamed *Lechevalieria* due to recent changes in classification. Actinomycetes of *Lechevalieria* and *Saccharothrix* have been recently developed as sources of various physiologically active compounds. Even though there are high possibilities to produce a variety of antibiotic compounds, antibiotic production from *Lechevalieria* species active against oomycete pathogens has not yet been reported.

It has been known that actinomycetes of *Lechevalieria* are mainly isolated from land soil containing high contents of organisms. Examples of antibiotics from *Lechevalieria* species including *Saccharothrix* include galacardin and saccharomicin having an antibacterial activity, karnamicin and formamicin having an antifungal activity, tetrazomine having an anticancer activity, and phosphonothrixin having a herbicidal activity.

Some butanoic acid derivatives having a physiological activity have been isolated from natural products or synthesized. For example, 3-(3-indolyl)-butanoic acid has been reported to have an antibacterial activity against *Ralstonia solanacearum* causing bacterial wilt. Further, 2-amino-2-methyl-butanoic acid has been reported to have an anticancer activity. However, so far, antifungal and antioomycete activities of butanoic acid derivatives have not yet been reported.

Phytophthora blight is a primary factor for decreases in the pepper production. In order to protect from such diseases, cultivation of resistant cultivars, crop rotation, biological control using an antifungal bacteria and the like have been performed. So far, the most effective control is a chemical control involving spraying of fungicides.

Examples of fungicides for control of Phytophthora blight in Korea include metalaxyl, fosetyl-Al, oxadixyl, propamocarb, copper oxychloride, chlorothalonil, dithianon and the like. Further, metalaxyl-copper oxychloride, metalaxyl-dithianone, oxadixyl-chlorothalonil and the like are used in combination. However, even though such active compounds have excellent efficacy, development of new compounds having different chemical structures and novel activities have been highly demanded due to appearances of chemical resistant strains of pathogens.

Therefore, development of environmentally friendly antifungals with low toxicity for control of phytophthora blight is urgently needed to replace such synthetic fungicides.

SUMMARY OF THE INVENTION

An object of the present invention is to provide the antibiotic thiobutacin which has a low toxicity to be suitable for control of plant diseases such as phytophthora blight and is an environmentally friendly product having a high biodegradability to be degraded naturally by other microorganisms.

Another object of the present invention is to provide an antifungal and antioomycete composition comprising thiobutacin for control of plant diseases.

In order to accomplish the above objects, the present invention provides the novel antibiotic thiobutacin expressed by the following formula 1 which is an actinomycete strain antibiotic and an antifungal and antioomycete composition containing the same as an effective ingredient for control of plant diseases. The present invention has been completed by analyzing a control efficacy against plant pathogen infections and an antimicrobial activity against phytophthora blight with thiobutacin of the present invention. Further, a control efficacy against phytophthora blight of thiobutacin of the present invention is compared with that of conventional fungicides in a growth room.

Formula 1

Preferably, thiobutacin of the present invention is isolated from *Lechevalieria aerocolonigenes* strain VK-A9 (deposit no. of microorganism: KCCM 10461, deposited in the Korean Culture Center of Microorganisms (Seoul, Korea) on Jan. 25, 2003 under the provisions of the Budapest Treaty on the International Recognition of the Deposit of Microorganisms).

Examples of plant diseases for which the antibiotic compositions of the present invention are usefully employed include those mediated by *Phytophthora capsici* and *Botrytis cinerea*.

BRIEF DESCRIPTION OF THE DRAWINGS

The invention is further illustrated with reference to the following non-limiting examples and FIGS. in which.

DESCRIPTION OF THE INVENTION

The inventors have extensively studied to develop bioactive, antifungal compounds from a variety of microorganisms such as actinomycete, bacteria, fungi and blue-green algae during last 10 years. As a result, a number of antagonistic actinomycetes, which produce antifungal, antibiotic compounds having an excellent antimicribial activity, have been developed.

The inventors have demonstrated bioactivities against various plant pathogen infections in agar medium after isolating about 1,500 types of actinomycetes from forests, lakes, fruit-growing soil, crop-growing soil, and the like in Kyeonggi-do and Chungnam areas, Korea. The inventors have discovered that *Lechevalieria aerocolonigenes* strain VK-A9 shows significant antioomycete activity against *Phytophthora capsici* and deposited the same in the Korean Culture Center of Microorganisms on Jan. 25, 2003 (deposit no. of microorganism: KCCM 10461).

The actinomycete strain VK-A9 developed in the present invention was identified to be *Lechevalieria aerocolonigenes* based on morphological, physiological and biochemical characteristics and 16S rDNA sequence analysis. It indicates that the actinomycete strain VK-A9 is a member of rare actinomycetes (see Table 1, set out hereinafter, as well as FIGS. 1A, 1B and 2)

Culture filtrates isolated and purified from antagonistic actinomycete *Lechevalieria aerocolonigenes* strain VK-A9 have been screened for antifungal or antimicrobial activity. As a result, one antibiotic of them is determined to have significant antimicrobial activity against *Phytophthora capsici*. The structure of the antibiotic was examined and named for thiobutacin.

The process for obtaining thiobutacin is described in detail hereafter. The antagonistic actinomycete *Lechevalieria aerocolonigenes* strain VK-A9 is cultured in a liquid broth containing carbon and nitrogen sources, and culture filtrates are applied to a column packed with HP-20 resin, which is eluted with MeOH. The fractions are extracted with EtOAc and further concentrated by application to a $C_{18}$ resin flash column and a silica gel flash column. The active fractions therefrom are further purified by Sephadex LH-20 column chromatography, which is eluted with MeOH. The active fractions therefrom are subsequently subjected to HPLC on a $C_{18}$ reversed-phase column to obtain the target antibiotic thiobutacin.

The novel antibiotic thiobutacin is isolated from antagonistic actinomycete *Lechevalieria aerocolonigenes* strain VK-A9 by the above method, and has the following formula 1.

Formula 1

As described above, some butanoic acid derivatives are known to have biological activities, such as antibacterial and anticancer activities. However, there are still little information about antifungal and antioomycete activity of butanoic acid derivatives. The present invention is the first instance of isolation of the antibiotic thiobutacin from the genus *Lechevalieria aerocolonigenes* active against plant oomycete pathogen.

In vitro antimicrobial activity against various plant pathogens and control efficacy of thiobutacin for the suppression of Phytophthora blight on pepper plants were evaluated under greenhouse conditions. As a result, the inventors have evaluated control efficacy of thiobutacin against plant pathogens, particularly *Phytophthora capsici* which is an oomycete and antifungal activity against *Botrytis cinerea* (see Table 5 hereinafter).

Figure 8:
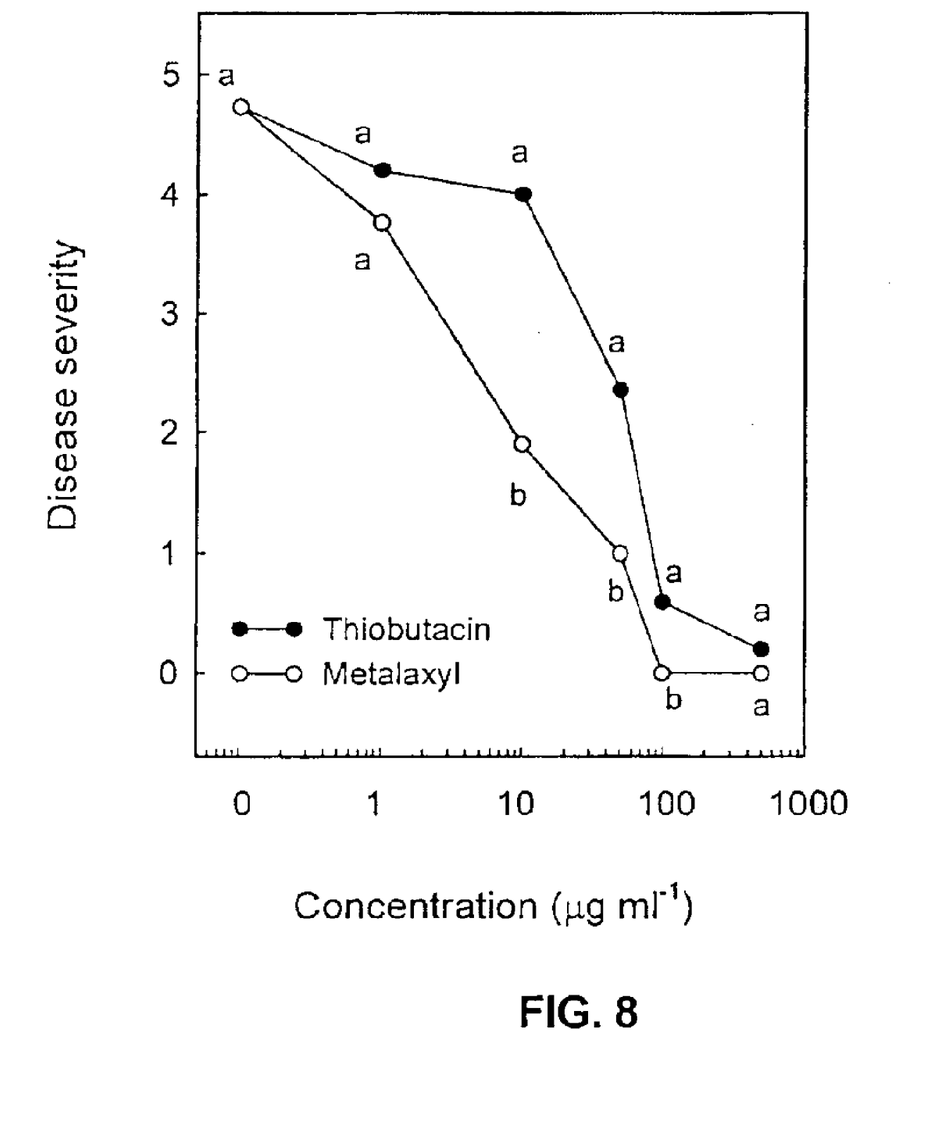
FIG. 8 is a graph representing the control efficacy of thiobutacin of the present invention against *Phytophthora capsici* infection in a growth room in comparison to the efficacy of the commercial fungicide metalaxyl.

Particularly, the inventors have conducted pot experiments under greenhouse conditions to express control efficacy of the antibiotic thiobutacin against plant pathogens and identified its activity by comparison with that of the commercial fungicide metalaxyl (FIG. 8). Therefore, environmental friendly antifungal and antioomycete compositions comprising the novel antibiotic thiobutacin as an efficient ingredient may be prepared and efficiently used for control of plant diseases.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

EXAMPLE 1

Isolation of Antagonistic Actinomycetes

Soil sample obtained from 10–20 cm depth of the outer layer was dried at a room temperature for 1 week to isolate antagonistic actinomycetes. The dried soil sample (1 g) was mixed with sterile distilled water and stirred in a rotary shaker at a rotational speed of 170 rpm for 1 hour to yield a soil suspension. The suspension was maintained at room temperature for 1 hour and supernatant therefrom was diluted with sterile distilled water at a ratio of 1:1000 (v:v). 1 ml of each suspension was plated on a Humic acid-Vitamin agar having a composition of 1.0 g humic acid, 0.5 g $Na_2HPO_4$, 1.71 g KCl, 0.05 g $MgSO_4.7H_2O$, 0.01 g $FeSO_4.7H_2O$, 0.02 g $CaCO_3$, 0.5 mg thiamine-HCl, 0.5 mg riboflavin, 0.5 mg niacin, 0.5 mg pyridoxin-HCl, 0.5 mg inositol, 0.5 mg Ca-pantothenate, 0.5 mg p-aminobenzoic acid, 0.25 mg biotin, 50 mg cycloheximide, 18 g agar, and 1 liter $H_2O$, adjusted to pH 7.2, wherein the vitamins and cycloheximide were filter-sterilized. The plate was cultivated at a temperature of 30° C. for 4 weeks to produce colonies.

Among colonies cultivated as described above, colonies which looked like antagonistic actinomycete were selected. These selected colonies were hard and had a substrate mycelium layer and aerial mycelium layer on the surface thereof, unlike others.

Antimicrobial activity of the selected actinomycete colonies was evaluated against *Phytophthora capsici, Collectrichum orbiculare, Magnaporthe grisea, Fusarium oxysporum, Rhizoctonia solani, Collectrichum gloeosporioides,* and *Alternaria mali.* The selected actinomycete colonies were single-streaked onto the center of a V8-juice agar plate (20% V8-juice, 18 g agar, 1 L distilled water, pH 6.4) and incubated at 28° C. for 4–10 days. A mycelial disk having a 5 mm diameter obtained from culture plants of plant pathogens such as *Phytophthora capsici, Collectrichum orbiculare* and the like was placed 30 mm from the center of the culture medium and additionally incubated for 7 days. The growth was determined.

On the other hand, the long-term maintenance of the selected antagonistic actinomycetes strain was as follows: For daily use, the strain was cultured in a yeast-malt agar (YMA, 10 malt extract, 4 g yeast extract, 4 g glucose, 18 g agar) filled in a glass test tube (10×28 mm). For a long-term maintenance, the strain was preserved in a yeast-malt extract broth containing 15% glycerol (v/v) at −70° C.

EXAMPLE 2

Physiological and Biochemical Characteristics, and 16S rDNA Sequence Analysis of Antagonistic Actinomycete Strain VK-A9

Antagonistic actinomycete strain VK-A9 produced aerial mycelium and substrate mycelium and was Gram-positive with Gram staining process. Morphological, chemotaxonomic, physiological and biochemical characteristics of the antagonistic actinomycete strain VK-A9 were examined using the methods of Bergey's Manual of Systematic Bacteriology and Bergey's Manual of Determinative Bacteriology.

For 16S rDNA sequence analysis of the antagonistic actinomycete strain VK-A9, 16S rDNA was isolated from chromosomal DNA and the sequence thereof was analyzed. The 16S rDNA sequence of the strain VK-A9 was aligned with reference sequences obtained from the databases of NCBI GenBank and the result was deposited in the databases of EMBL GenBank under accession number AY196703 (SEQ ID NO: 1).

The morphological characteristics of the antagonistic actinomycetes strain VK-A9 were examined by 6 ISP (International *Streptomyces* Project) culture media and nutrient agar and Bennett's agar medium.

The strain VK-A9 grew well on the above culture media except peptone-yeast extract iron agar (ISP-6 medium). Aerial mycelia were produced from all the culture media and the color thereof was white or pale yellow. Substrate mycellium occasionally produced was pale yellow or pale brown in color. While the strain produced light brown soluble pigment in the Tyrosine agar (ISP-7 medium), no soluble pigments were produced in the other media.

Figure 1A:
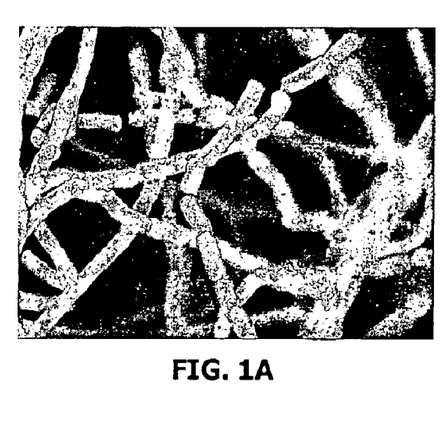
FIGS. 1A and 1B are SEM (scanning electron microscope) micrographs of spore chain morphology (FIG. 1A) and pseudosporangium (FIG. 1B) of *Lechevalieria aerocolonigenes* strain VK-A9 according to the present invention.
Figure 1B:
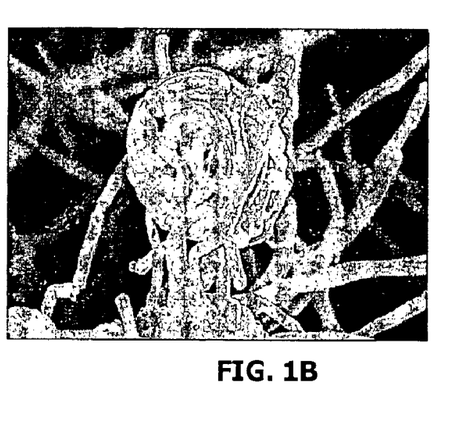

The spore chains of strain VK-A9 were confirmed with the scanning electron microscope (FIG. 1A). The strain VK-A9 was observed to have long and slender spores of cylindrical forms on aerial mycelia (0.3–0.6×0.8–1.6 μm in size) with a smooth surface ornament. The spore chains of strain VK-A9 contained eight to fourteen spores of straight or slightly flexuous types. A special structure such as pseudosporangium was also observed (FIG. 1B).

In order to determine an isomer of diaminopimelic acid (DAP) which is one of structural materials of the cell wall, it was noted that whole cell hydrolysates of strain VK-A9 contained meso-diaminopimelic acid as the only amino acid of the peptidoglycan by analyzing the structural materials of the cell wall of the strain VK-A9.

Galactose, rhamnose and mannose were whole cell sugars in the strain VK-A9, whereas arabinose, madurose or xylose was not detected. These results indicated that the strain VK-A9 belonged to cell wall type III and the whole cell sugar pattern type E. The major menaquinone of the strain VK-A9 was confirmed to be tetrahydrogenated menaquinone with nine isoprene units [MK-9($H_4$)]. No mycolic acids were present. Based on the facts, it is noted that the strain VK-A9 is not general *Streptomyces* but genus *Lechevalieria*, which is a member of rare actinomycetes.

The strain VK-A9 hydrolyzed casein, esculin, gelatin, hypoxanthine, starch, tyrosine and urea, but not adenine, hippurate and xanthine. Nitrate reduction occurred in the medium amended with $KNO_3$ and phosphatase activity was detected. The strain VK-A9 grew well at temperatures between 10 and 37° C., but no growth occurred at 45° C. The strain VK-A9 tolerated up to 4% (w/v) NaCl in the basal medium. This microorganism utilized citrate but did not oxalate and DL-tartrate. Acids were produced from L-arabinose, cellobiose, dextrin, glucose, glycerol, inositol, lactose, melibiose, L-rhamnose, salicin, sucrose and D-xylose.

Based on the morphological, chemotaxonomic, physiological and biochemical characteristics, the strain VK-A9 was identified to be *Lechevalieria aerocolonigenes*, compared to the data of *L. aerocolonigenes*. These results were again identified through the data of the 16S rDNA sequence analysis.

Figure 2:
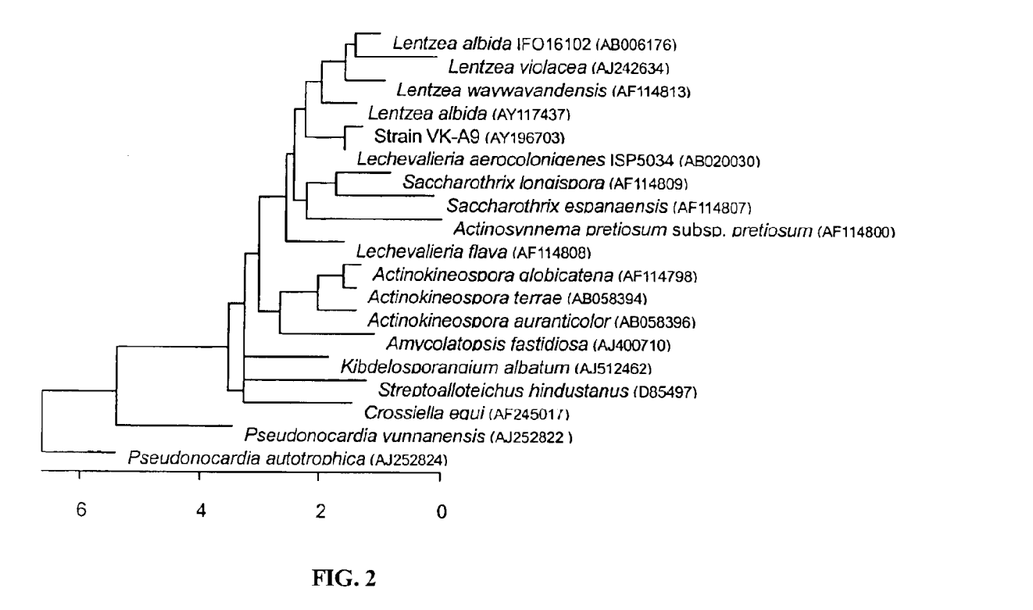
FIG. 2 is a phylogenetic tree determined by a 16S rDNA sequence analysis of *Lechevalieria aerocolonigenes* strain VK-A9 according to the present invention.

The phylogenetic tree determined by the clustal method showed that *Lechevalieria aerocolonigenes* was most closely related to the strain VK-A9 (FIG. 2). The 1,474 of 1,476 16S rDNA nucleotide sequences of the strain VK-A9 were identical to those of *Lechevalieria aerocolonigenes* ISP 5034 (EMBL/GenBank accession number: AB020030), indicating that the sequence similarity of 16S rDNA of the two actinomycetes was 99.9%.

It is noted that the antagonistic actinomycetestrains strain VK-A9 of the present invention is identified to be *Lechevalieria aerocolonigenes* strain with the result of the morphological, chemotaxonomic, physiological and biochemical characteristics and the 16S rDNA sequence analysis.

TABLE 1

Physiological and biochemical characteristics of the antagonistic actinomycete strain VK-A9

| Characteristic | Strain VK-A9 | *Lechevalieria aerocolonigenes*[a] |
|---|---|---|
| Formation of aerial mycelium | +[b] | + |
| Fragmentation of substrate mycelium | + | + |
| Diagnostic diaminopimelic acid isomer | meso-DAP | meso-DAP |
| Whole cell sugar composition | Galactose, rhamnose and mannose | Galactose and rhamnose |
| Mycolic acid | − | − |
| Predominant menaquinone | MK-9(H$_4$) | MK-9(H$_4$) |
| Hydrolysis of | | |
| Casein | + | + |
| Esculin | + | + |
| Gelatin | + | + |
| Starch | + | + |
| Urea | + | + |
| Xanthine | − | − |
| Reduction of nitrate | + | + |
| Phosphatase | + | + |
| Growth at | | |
| 10° C. 37° C. | + | + |
| 45° C. | − | − |
| Growth at NaCl | | |
| 2% | + | + |
| 4% | + | + |
| 5% | − | − |
| Utilization of | | |
| Citrate | + | + |
| Oxalate | − | + |
| DL-Tartrate | − | + |
| Acid production from | | |
| L-Arabinose | + | + |
| Cellobiose | + | + |
| Glucose | + | + |

TABLE 1-continued

Physiological and biochemical characteristics of the antagonistic actinomycete strain VK-A9

| Characteristic | Strain VK-A9 | *Lechevalieria aerocolonigenes*[a] |
|---|---|---|
| Inositol | + | + |
| Sucrose | + | + |
| D-Xylose | + | + |

[a]Results from the data of Labeda (18) and Williams et al. (48).
[b]Symbols: +, positive; −, negative; V, variable (11–89% of strains are positive).

EXAMPLE 3

Detection of Antimicrobial Activity

1) Antimicrobial Activity Against Various Plant Fungal and Oomycete Pathogens

The *Lechevalieria aerocolonigenes* strain VK-A9 showed strong antifungal and antimicrobial activity against and further, remarkably inhibited the growth of the fungi and oomycete *Phytophthora capsici, Alternaria mali, Colletotrichum orbiculare, Colletotrichum gloeosporioides, Magnaporthe grisea*, and *Rhizoctonia solani*, as described in Table 2.

TABLE 2

Antimicrobial activity of the *Lechevalieria aerocolonigenes* strain VK-A9 against various plant fungal and oomycete pathogens

| Plant pathogenic fungi and oomycetes | Blocked length(mm) |
|---|---|
| *Alternaria mali* | 20 |
| *Colletotrichum gloeosporioides* | 18 |
| *Colletotrichum orbiculare* | 28 |
| *Magnaporthe grisea* | 20 |
| *Phytophthora capsici* | 22 |
| *Rhizoctonia solani* | 15 |

However, the *Lechevalieria aerocolonigenes* strain VK-A9 exhibited no inhibitory activity against *Bacillus subtilis, E. coli*, and *Ralstonia solanacearum*.

2) Antimicrobial Activity of Antibiotic Crude Extracts Produced from the *Lechevalieria aerocolonigenes* Strain VK-A9

Antibiotic crude extracts were prepared to predetermine antimicrobial activity of the selected antagonistic actinomycete strains by the following method.

Fermentation of each antagonistic actinomycete strain was carried out at 28° C. for 10 days in a glycerol peptone broth (GPB: 20 g glycerol, 10 g polypeptone, 5 g meat extract, 1 L distilled H$_2$O, pH 7.0 before autoclaving). The culture solution were centrifuged or filtered to remove cells. The culture filtrate was extracted with EtOAc with the same volume of the filtrates three times. The EtOAc layers were combined and concentrated in vacuo to dryness. The residue was dissolved with minimum amount of MeOH and was stored at −20° C.

Bioassay for antimicrobial activity of the crude extracts of the antagonistic actinomycete strain was conducted by the following method.

Bioassay of the crude extracts of the antagonistic actinomycete strain was performed by a paper disk-agar diffusion method in agar inoculated with *Phytophthora capsici* and *Collectrichum orbiculare*.

"For *Phytophthora capsici*, V8-juice agar was mixed with zoospore suspension ($10^6$ zoospore/ml) of *Phytophthora capsici* to give a bioassay plate. For *Collectrichum orbiculare*, spore suspension ($10^6$ spore/ml) was mixed with liquid potato dextrose agar (potato dextrose broth 20 g, agar 10 g, $H_2O$ IL) to give a bioassay plate. The paper disk (7 mm) wetted with the crude extracts was dried at a room temperature for 2 hours and placed on the agar media inoculated with test pathogenic bacteria. After incubating the above plate at 28° C. for 24 to 72 hours, bacterial growth inhibition was determined by a diameter of the produced clear zone. The result is described in Table 3. It is noted that the *Lechevalieria aerocolonigenes* strain VK-A9 have in vitro distinctive antimicrobial activity against *Phytophthora capsici* and *Collectrichum orbiculare*."

TABLE 3

Mycelial growth inhibition of the crude extracts of *Lechevalieria aerocolonigenes* strain VK-A9

|  | Phytophthora capsici | Collectrichum orbiculare |
|---|---|---|
| Diameter of blocking circle(mm) | 28 ± 1.5 | 25 ± 0.8 |

* Paper disk having 7 mm of diameter wetted with 5 ml of the crude extracts was placed on the test agar.

EXAMPLE 4

Culture Conditions of the *Lechevalieria aerocolonigenes* Strain VK-A9 for the Production of Antibiotics In order to obtain optimal culture conditions of the *Lechevalieria aerocolonigenes* strain VK-A9 for the production of antibiotic materials, the production of antibiotics were determined using 4 different broths with various culture times, wherein the broths were starch casein broth (SCB), starch glucose broth(SGB), glycerol dextrin broth (GDB) and glycerol peptone broth(GPB).

After 4 days of incubation, the culture filtrate from each broth were applied to a column packed with Diaion HP-20 resin, which was eluted with stepwise gradients of aqueous MeOH (0 to 100%) every 2 days until 14 days of incubation. Activity against *Cladosporium cucumerinum*, *Phytophthora capsici*, and *Rhizoctonia solani* was determined.

Figure 3:
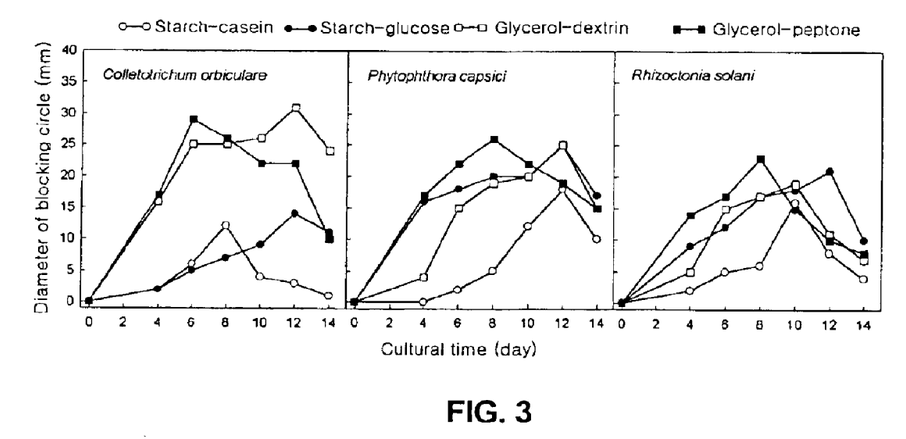
FIG. 3 is a graph representing an inhibitory activity of the antibiotic of the present invention against plant pathogens according to culture medium composition and cultural time (time period of culturing)
Figure 4:
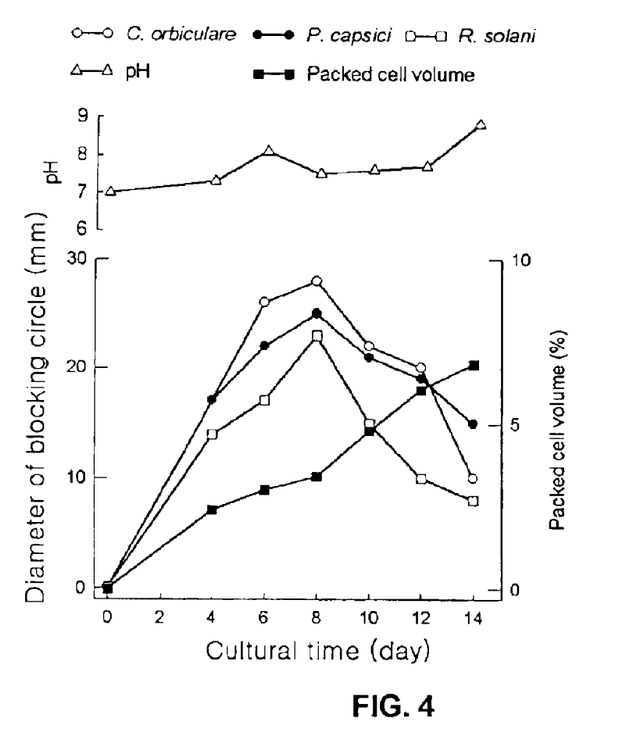
FIG. 4 is a graph representing an inhibitory activity and changes in production of the antibiotic of the present invention with cultural time in a glycerol peptone broth.
Figure 5:
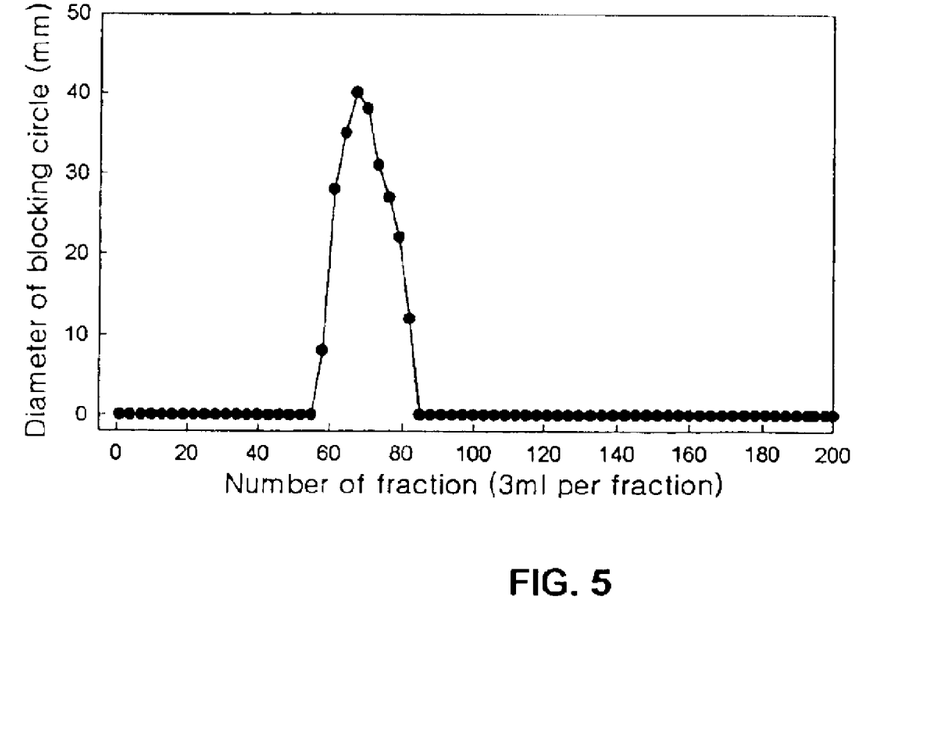
FIG. 5 is a graph representing an inhibitory activity against Phytophthora blight of antibiotic fractions eluted through Sephadex LH-20 column chromatography according to the present invention.

As a result, the production of antibiotics was increased with the time of incubation in each broth and particularly, the maximum antimicrobial activity was exhibited with the glycerol peptone broth (GPB) after 8 days of incubation, which indicated the maximum production of antibiotics (FIG. 3)

pH was repeatedly increased and decreased during the incubation in the glycerol peptone broth (GPB), which indicated that the production of antibiotics was related to pH changes. Amount of microorganism was continuously increased for 14 days of incubation (FIG. 4).

The optimal culture condition of the *Lechevalieria aerocolonigenes* strain VK-A9 for the production of antibiotics was 8 days of incubation in the glycerol peptone broth (GPB). A total of 78 liters were cultivated.

The detailed composition of broths used in the production of antibiotics of the *Lechevalieria aerocolonigenes* strain VK-A9 is described below.

Glycerol Dextrin Broth (GDB)

| Glycerol | 20 g |
|---|---|
| Dextrin | 20 g |
| Soyton | 10 g |
| Yeast extracts | 3 g |
| $(NH_4)_2SO_4$ | 2 g |
| $K_2HPO_4$ | 4 g |
| Distilled water | 1 L |

Glycerol Peptone Broth (GPB)

| Glycerol | 20 g |
|---|---|
| Polypeptone | 10 g |
| Meat extracts | 10 g |
| Distilled water | 1 L |

Starch Casein Broth (SCB)

| Soluble starch | 20 g |
|---|---|
| Trypton peptone | 0.6 g |
| Starch | 10 g |
| $K_2HPO_4$ | 4 g |
| $KNO_3$ | 4 g |
| NaCl | 4 g |
| $MgSO_4 \cdot 7H_2O$ | 1 g |
| $FeSO_4 \cdot 7H_2O$ | 20 mg |
| $CaCO_3$ | 40 mg |
| Distilled water | 1 L |

Starch Glucose Broth (SGB)

| Soluble starch | 10 g |
|---|---|
| Glucose | 10 g |
| Yeast extracts | 5 g |
| Casamino acid | 5 g |
| Distilled water | 1 L |

EXAMPLE 5

Isolation and Purification of Antibiotic Thiobutacin

After 5 ml of inoculum of the *Lechevalieria aerocolonigenes* strain VK-A9 cultured in a yeast-malt extract agar (YMA) (100 ml) at 28° C. for 2 days was inoculated in 500 ml of a glycerol peptone broth in a 1 L of flask, the result was incubated in a rotary shaker at a rotational speed of 170 rpm at 28° C. for 10 days. 78 L of the culture medium was centrifuged at 30,000 g for 10 minutes to separate supernatant and microorganism. The supernatant was applied to a column packed with 6 L of Diaion HP-20 resin, which was eluted with stepwise gradients of aqueous MeOH (0 to 100%).

Figure 6:
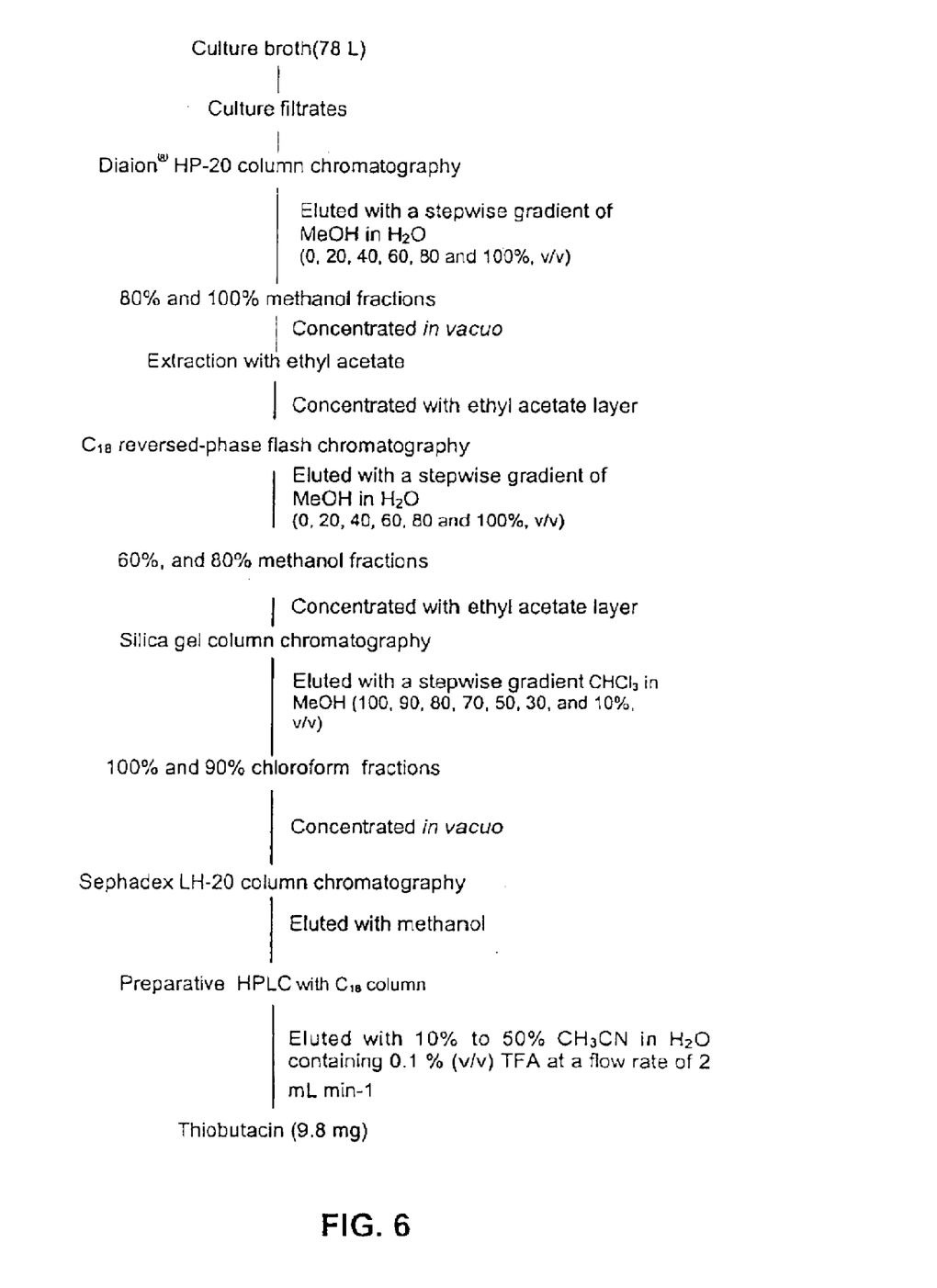
FIG. 6 is a flowchart representing purification procedures of thiobutacin from the culture filtrates of *Lechevalieria aerocolonigenes* strain VK-A9 according to the present invention.

Further, purification of the antibiotic was carried out by the process described in FIG. 6. The 80% and 100% MeOH, which seemed to show the antimicrobial activity, was collected and concentrated in vacuo. The residue was extracted with EtOAc with the same volume thereof. The organic layers were combined and concentrated in vacuo. The residue was subjected to $C_{18}$ reversed-phase flash column, which was eluted with stepwise gradients of aqueous MeOH (0 to 100%). The 60% and 80% MEOH fractions showed the antimicrobial activity.

The active fractions were absorbed on a silica gel flash column (CHCl$_3$:MeOH, 100:0 to 10:90). The 100% and 90% CHCl$_3$ fractions were purified by Sephadex LH-20 column chromatography with eluting 100% MeOH. Partial fractions from 31$^{th}$ to 52$^{nd}$, among 300 fractions, were further purified by Sephadex LH-20 column chromatography.

The active fractions from 57$^{th}$ to 81$^{st}$ in the Sephadex LH-20 column chromatography were subsequently subjected to HPLC on a C$_{18}$ reversed-phase column at UV 227 nm. The column was eluted with a linear gradient from 10% aqueous CH$_3$CN containing 0.1% (v/v) TFA to 50% aqueous CH$_3$CN containing 0.1% (v/v) TFA. The fractions at a retention time of 24.03 min showed an inhibitory activity against *Phytophthora capsici*. Antibiotics in these fractions showed a single peak when they were eluted with various organic system on HPLC.

The active fractions were concentrated in vacuo to produce 9.8 mg of brownish oily powder. The UV absorption maxima ($\lambda_{max}$) of the antibiotics were shown at 227, 260 and 360 nm in MeOH.

EXAMPLE 6

Identification of Structure of the Antibiotic Thiobutacin

Structure of the antibiotics isolated and purified above was determined by the analyses of mass and NMR spectral data.

The NMR spectral data was determined using a Bruker AMX 500 NMR spectrometer.

The antibiotics dissolved in CD$_3$OD were conducted for $^1$H NMR □ $^{13}$C NMR spectroscopy, DEPT experiment to identify "multiplicity" (quaternary, CH, CH$_2$ or CH$_3$), and 2D-NMR spectral studies to identify the correlations between protons and between proton and carbon.

For 2D-NMR spectral studies, the antibiotic dissolved in CD$_3$OD was conducted for $^1$H—$^1$H and $^1$H—$^{13}$C COSY spectroscopy, HMBC, HMQC, HSQC, ROESY and NOESY spectroscopy.

The EI high-resolution mass spectrometry of the antibiotic was conducted to identify its molecular weight and composition ratio of carbon, nitrogen and oxygen by employing a JEOL HX 100A-HX100A Tandem mass spectrometer.

Figure 7:
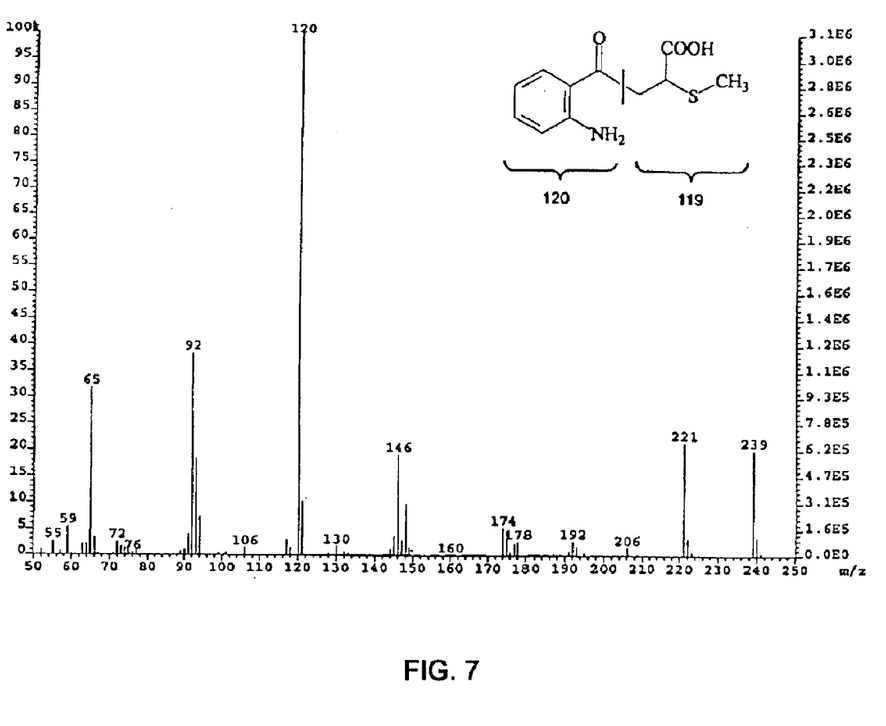
FIG. 7 is a graph representing EI mass spectrum of the antibiotic thiobutacin according to the present invention.

The EI mass spectrum of the antibiotic thiobutacin confirmed its molecular weight to be 239 and its formula to be C$_{11}$H$_{13}$NO$_3$S (FIG. 7). The proton and carbon counts from $^1$H and $^{13}$C NMR spectra and DEPT experiment indicated that the 13 protons and 11 carbons are present, thus supporting the molecular formula. The NMR analysis of thiobutacin is summarized in the following Table 4.

TABLE 4

NMR spectra data of thiobutacin produced from the *Lechevalieria aerocolonigenes* strain VK-A

| Carbon no. | $^{13}$C, δ$^a$ | $^1$H, δ$^b$(m$^c$, J in Hz) |
|---|---|---|
| 1 | 117.6 | — |
| 2 | 160.1 | — |
| 3 | 117.8 | 6.92(br d, 1.0, 8.3) |
| 4 | 134.1 | 7.33(dt, 1.6, 7.5, 8.3) |
| 5 | 120.0 | 6.87(br t, 1.0, 7.5, 7.8) |
| 6 | 131.6 | 7.41(dd, 1.6, 7.8) |

TABLE 4-continued

NMR spectra data of thiobutacin produced from the *Lechevalieria aerocolonigenes* strain VK-A

| Carbon no. | $^{13}$C, δ$^a$ | $^1$H, δ$^b$(m$^c$, J in Hz) |
|---|---|---|
| 2' | 173.7 | — |
| 4' | 79.4 | 4.81(m) |
| 5' | 33.8 | 3.29(dd, 11.0, 7.8) |
|   |   | 3.45(dd, 11.0, 8.8) |
| 2" | 64.3 | 3.77(dd, 11.2, 6.0) |
|   |   | 3.80(dd, 11.2, 5.2) |

$^a$125 MHz, chemical shift in ppm.
$^b$500 MHz, chemical shift in ppm.
$^c$Abbreviations of signal multiplicity are dd: doublet of doublets, dt: doublet of triplets, br d: broad doublet, brt: broad triplet, m: multiplet, The $^1$H NMR spectrum indicated the presence of methine groups at δ 6.60, δ 6.73, δ 7.23 and δ 7.78. Based on the $^{13}$C NMR spectrum, the presence of aromatic carbons was confirmed at the positions of δ 115.0, δ 117.0, δ 130.8 and δ 134.3 and an amine group at δ 151.4. The carbonyl group was detected at the position of δ 199.2 in $^{13}$C NMR spectrum. These results suggested that the structure of the antibiotic contained an aromatic group attached with an amine and a carbonyl moiety. Following the analysis of $^1$H NMR spectrum, the presence of a methylene group was confirmed at δ 3.27 and δ 3.66. This methylene group was also detected at the position of δ 41.0 in $^{13}$C NMR spectrum. The carbon resonance at δ 42.9 indicated the presence of a carbon atom attached with a carboxylic acid group resonated at δ 174.9 in $^{13}$C NMR spectrum. The presence of a methyl group bearing a sulfur atom was confirmed at the position of δ 2.23 in $^1$H NMR and δ 13.2 in $^{13}$C NMR spectrum, respectively.

The HMBC spectrum also showed the correlations of this carbonyl carbon (δ 199.2, C-7) with methylene protons (δ 3.27, δ 3.66, H-8) and carbonyl carbon (δ 199.2, C-7) with aromatic protons (δ 7.78, H-6). The correlations of carboxylic acid carbon (δ 174.9) with methylene protons (δ 3.27, δ 3.66, H-8) were confirmed by HMBC spectral analysis. The HMBC spectral analysis revealed the correlations of sulfur-bearing methyl carbon (δ 13.2) with a proton (δ 3.71, H-9).

Based on all the spectral data, the chemical structure of the antibiotic, which turned out to be a novel antibiotic, was determined to be 4-(2-aminophenyl)-4-oxo-2-methylthio-butanoic acid (molecular formula C$_{11}$H$_{13}$NO$_3$S) as a butanoic acid derivative. The inventors of the present invention named this novel antibiotic for thiobutacin.

Formula 1

EXAMPLE 7

Antimicrobial Activity of Antibiotic Thiobutacin Against Various Plant Pathogen Infections Plant pathogens such as oomycete, yeasts, and bacteria, for example, *Phytophthora capsici, Alternaria mali, Botrytis cinerea, Cladosporium cucumerinum, Colletotrichum orbiculare, Fusarium oxysporium* f. sp. cucumerinum, *Mag-* naporthe grisea, Rhizoctonia solani and the like, were cultivated in a potato dextrose agar or nutrient agar.

The antibiotic thiobutacin was mixed with 1% of potato dextrose agar. The antibiotic thiobutacin in methanol, ranging in concentration from 0 to 100 μg ml$^{-1}$, was dispensed into microfiter plates. Each spore or zoospore suspension having a concentration of 10$^5$ spore/ml was placed in each well. After incubation of inoculated microtiter dish at 28° C. for 4 days, minimum inhibitory concentrations (MICs) of thiobutacin, which is the least amount of antibiotic that prevents growth of the microorganism, was determined. The result is summarized in Table 5.

TABLE 5

Minimum inhibitory concentrations (MICs) of thiobutacin for various microorganism growthes

| Microorganism | MIC (μg ml$^{-1}$)$^a$ |
|---|---|
| *Alternaria mali* | >100$^b$ |
| *Botrytis cinerea* | 50 |
| *Cladosporium cucumerinum* | 50 |
| *Colletotrichum orbiculare* | >100 |
| *Fusarium oxysporum* f.sp. *cucumerinum* | >100 |
| *Magnaporthe grisea* | >100 |
| *Phytophthora capsici* | 10 |
| *Rhizoctonia solani* | >100 |
| *Candida albicans* | >100 |
| *Saccharomyces cerevisiae* | 30 |
| *Bacillus subtilis* | >100 |
| *Erwinia carotovora* subsp. *carotovora* | >100 |
| *Ralstonia solanacearum* | >100 |
| *Xanthomonas campestris* pv. *Vesicatoria* | >100 |

$^a$The lowest concentration of the antibiotic thiobutacin required for complete inhibition of microbial growth.
$^b$The value of >100 represents that growth of the microorganisms was not completely inhibited at 100 μg ml$^{-1}$ of the antibiotic thiobutacin.

The thiobutacin showed the most sensitive antimicrobial activity against *Phytophthora capsici*. The antibiotic thiobutacin also inhibited the mycelial growth of *B. cinerea* and *C. cucumerinum* at 50 μg ml$^{-1}$. However, the growth of *Alternaria mali, Colletotrichum orbiculare, Fusarium oxysporum* f. sp. *cucumerinum, Magnaporthe grisea, Rhizoctonia solani* was not inhibited.

EXAMPLE 8

Comparison in Control Efficacy of the Antibiotic Thiobutacin vs. the Commercial Fungicide Metalaxyl The commercial fungicide metalaxyl was used to compare the antifungal activity with thiobutacin against *Phytophthora capsici* infection on pepper plants in a growth room. Before the pepper plant was inoculated with *Phytophthora capsici* infection, disease severity was determined both for each treated with various concentrations of thiobutacin and metalaxyl and for the untreated control. Disease severity on pepper plants was rated daily after inoculation based on a scale 0–5:

0=no visible disease symptoms;

1=leaves slightly wilted with brownish lesions beginning to appear on stems;

2=30–50% of entire plant diseased;

3=50–70% of entire plant diseased;

4=70–90% of entire plant diseased; and

5=plant dead.

From 4 days after inoculation, branches of the pepper plant not treated with chemicals exhibited the disease development in the leaves, while the pepper plants treated with thiobutacin and metalaxyl did not exhibit any symptoms.

From 5 days after inoculation, the pepper plants treated with 10 μg/ml of thiobutacin and 50 μg/ml of metalaxyl exhibited the disease development in the leaves. The pepper plants treated with 10 μg/ml of metalaxyl exhibited slight disease symptoms. After 10 days, the pepper plant not treated with chemicals completely died. The pepper plants treated with 500 μg/ml of thiobutacin did not show any phytophthora infection and those with 100 μg/ml exhibited slight damages (FIG. 8). The pepper plants treated with higher concentrations than 100 μg/ml of metalaxyl did not show any phytophthora development.

In conclusion, the novel antibiotic thiobutacin of the present invention, produced by *L. aerocolonigenes* strain VK-A9, not only demonstrates an efficacy for controlling Phytophthora disease on pepper to almost the same efficacy as exhibited by the organic synthetic fungicides, but it also possess a high biodegradability as a naturally occurring antibiotic.

The antibiotics of the present invention may be used alone or in combination with fillers, solvents, dispersants, adjuvants, and other additives normally used by those of skill in the art. That is, the antibiotics of the present invention may be used as antimicrobial and antifungal agents by producing compositions comprising antibiotics of the present invention as an active ingredient.

Further, the antibiotic thiobutacin of the present invention is very useful in developing agricultural fungicides, because of its significant control efficacy against plant pathogen infections such as *Phytophthora capsici, Botrytis cinerea*, and the like.

What is claimed is:

1. An isolated and purified compound of the formula:

2. A composition comprising the compound as claimed in claim 1 and at least one additional component selected from the group consisting of solvents, fillers, dispersants and adjuvants.

3. A process for preparing the compound as claimed in claim 1, comprising the steps of culturing *Lechevalieria aerocolonigenes* strain VK-A9 in a liquid culture medium containing carbon and nitrogen sources, at 20 to 40° C. under aerobic conditions, to cause the *Lechevalieria aerocolonigenes* strain VK-A9 to produce said compound, recovering from the culture medium a culture filtrate including said compound, and isolating and purifying said compound from said culture filtrate.

4. The process of claim 3, wherein isolation and purification of said compound from said culture filtrate comprises the steps of:
    applying the culture filtrate to a column packed with polystyrene divinylbenzene copolymer resin;
    eluting the column with MeOH, triturating with EtOAc, and concentrating the resultant material;
    conducting the resultant material through a $C_{18}$ reversed-phase flash column and a silica gel flash column;
    purifying the active fractions of the resultant material by hydroxypropylated cross-linked dextran column chromatography eluting with MeOH;
    further, purifying the active fractions of the resultant material by high performance liquid chromatography on a $C_{18}$ reversed-phase column, to yield said isolated and purified compound.

5. The process of claim 4, wherein said column packed with polystyrene divinylbenzene copolymer resin is eluted in successive steps including an elution with an 80% (v/v) MeOH aqueous solution, followed by an elution with 100% MeOH.

6. The process of claim 4, wherein said $C_{18}$ reversed-phase flash column is eluted in successive steps including an elution with a 60% (v/v) MeOH aqueous solution, followed by an elution with an 80% (v/v) MeOH aqueous solution.

7. The process of claim 4, wherein said silica gel flash column is eluted in successive steps including an elution with CHCl$_3$, followed by elution with a 90:10 (v/v) mixture of CHCl$_3$:MeOH.

8. The process of claim 4, wherein said hydroxypropylated cross-linked dextran column chromatography is eluted with MeOH.

9. The process of claim 4, wherein said HPLC on a C$_{18}$ reversed-phase column is eluted with an aqueous CH$_3$CN composition containing trifluoroacetic acid.

10. The process of claim 4, wherein said liquid culture medium is a glycerol peptone broth.

11. A method of combating plant disease attributable to a microorganism selected from the group consisting of *Botrytis cinerea, Cladosporium cucumeranum, Phytophthora capsici, Saccharomyces cerevisiae, Auernaria mali, Colletotrichum gloeosporioides, Colletotrichum orbiculare, Magnaporthe grisea,* and *Rhizoctonia solani*, in a plant having or susceptible to such plant disease, said method comprising administering to said plant an effective amount of a compound as claimed in claim 1.

12. The method of claim 11, wherein said plant disease is phytophthora blight.

13. The method of claim 11, wherein said microorganism is selected from the group consisting of *Phytophthora capsici* and *Botrytis cinerea*.

14. The method of claim 11, wherein said plant disease is mediated by *Phytophthora capsici*.

\* \* \* \* \*